US008771241B2

(12) United States Patent
Buntel

(10) Patent No.: US 8,771,241 B2
(45) Date of Patent: Jul. 8, 2014

(54) VISUALLY ALIGNING DISPENSING UNIT

(71) Applicant: Empire Technology Development LLC, Wilmington, DE (US)

(72) Inventor: Christopher John Buntel, Singapore (SG)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/939,915

(22) Filed: Jul. 11, 2013

(65) Prior Publication Data

US 2013/0310775 A1 Nov. 21, 2013

Related U.S. Application Data

(63) Continuation of application No. 13/994,438, filed as application No. PCT/US2013/030107 on Mar. 11, 2013.

(60) Provisional application No. 61/612,663, filed on Mar. 19, 2012.

(51) Int. Cl.
*A61M 35/00* (2006.01)

(52) U.S. Cl.
USPC .......................................... 604/302; 604/300

(58) Field of Classification Search
CPC .............................. A61F 9/0026; A61F 9/0008
USPC ........................................ 604/300, 302, 295
See application file for complete search history.

(56) References Cited

U.S. PATENT DOCUMENTS

| 4,733,802 A | 3/1988 | Sheldon |
| 5,558,653 A | 9/1996 | Lindstrom |
| 5,810,794 A | 9/1998 | Peplinski |
| 5,932,206 A * | 8/1999 | Pine et al. ................. 424/78.04 |
| 6,371,945 B1 | 4/2002 | Sherman |
| 2010/0211027 A1* | 8/2010 | Pine .............................. 604/290 |
| 2010/0283957 A1 | 11/2010 | Matera et al. |
| 2011/0098664 A1 | 4/2011 | Rehkemper et al. |

FOREIGN PATENT DOCUMENTS

GB 2142829 A 2/1984

OTHER PUBLICATIONS

International Search Report and Written Opinion for PCT/US2013/030107 dated May 17, 2013.
E-Z Drops Application Strips, http://ezdrops.com/files/10380464.pdf (May 25, 2011).
Glaucoma News, http://www.allaboutvision.com/conditions/glaucoma_news.htm (Nov. 2012).

(Continued)

*Primary Examiner* — Susan Su
(74) *Attorney, Agent, or Firm* — Pepper Hamilton LLP

(57) ABSTRACT

Dispensing units and methods for using dispensing units to apply eye drops to an eye of a user are disclosed. A dispensing unit may include a dispensing barrel having a dispensing orifice and one or more concentric rings. A particular dispensing unit has one concentric ring that is disposed around the circumference of the dispensing barrel and is configured to permit a user to properly visually align the dispensing barrel above an eye of the user. An alternate dispensing unit has first and second rings disposed around a circumference of the dispensing barrel that are configured to permit a user to properly visually align the dispensing barrel above an eye of the user by one or more of color mixing or polarization techniques.

23 Claims, 3 Drawing Sheets

(56) References Cited

OTHER PUBLICATIONS

Hennessy et al., Videotaped Evaluation of Eyedrop Instillation in Glaucoma Patients with Visual Impairment or Moderate to Severe Visual Field Loss, *Ophthalmology* (Dec. 2010), 117(12):2345-2352 (Abstract).

Wilson Ophthamolic, http://www.hilco.com/default.asp (Jun. 4, 2013).

* cited by examiner

_US 8,771,241 B2_

VISUALLY ALIGNING DISPENSING UNIT

CLAIM OF PRIORITY

The present application is a continuation application of U.S. patent application Ser. No. 13/994,438, filed Jun. 14, 2013 entitled "Visually Aligning Dispensing Device," which in turn claims the benefit of and priority to U.S. national stage filing under 35 U.S.C. §371 of International Application No. PCT/US2013/030107 filed Mar. 11, 2013 entitled "Visually Aligning Dispensing Device," which in turn claims the benefit of and priority to U.S. Provisional Application Ser. No. 61/612,663, entitled "Visually Aligning Dispensing Unit," which application was filed on Mar. 19, 2012. Each of the aforementioned applications is incorporated by reference herein in its entirety and for all purposes.

BACKGROUND

Conventional dispensing units are imprecise and difficult to properly align with the user's eyeball. As a result, eye drops are frequently improperly delivered. For example, eye drops may land on a user's cheek, eyebrow, or forehead. This can result in frustration for the user, cosmetic attention to remove the improperly delivered eye drops, and wasted fluid. With prescription eye drops in particular, this wasted fluid can affect the deliverable quantity of medicine and effectively raise the unit price of the medicine.

The above-listed problems may be particularly acute for elderly patients and those with compromised eyesight. A recent study indicated that only 71% of glaucoma patients were able to deliver eye drops into their eye, and only 39% of those patients did so without physically touching the bottle to the surface of the eye. As such, more efficient and practical ways of delivering eye drops would be desirable.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a dispensing unit may include a dispensing barrel having a dispensing orifice, and one concentric ring disposed around a circumference of the dispensing barrel. The concentric ring is configured to permit a user to properly visually align the dispensing barrel above an eye of the user.

In an embodiment, a dispensing unit may include a dispensing barrel having a dispensing orifice, and a plurality of concentric rings disposed around a circumference of the dispensing barrel. The plurality of concentric rings may include a first concentric ring and a second concentric ring located proximal to the reservoir as compared to the first concentric ring. The plurality of concentric rings are configured to permit a user to properly visually align the dispensing barrel above an eye of the user.

DETAILED DESCRIPTION

As used herein, the term "dispensing unit" refers to dispensing bottles, single-use eye drop dispensers, eye droppers and/or any other device or portion of a device designed to enable the application of a fluid to the eye.

The present disclosure describes numerous embodiments for delivering eye drops effectively to a user. As disclosed herein, conventional dispensing units may be modified to be configured with at least one concentric ring located around the circumference of the dispensing unit barrel (i.e., the barrel of the syringe) to aid in proper alignment of the barrel to the user's eye. Single or double colored rings may be used. For example, two differently colored rings may be used and appear as a third "new" colored single ring when the dispensing unit is properly aligned. Alternatively, two transparent rings having different optical polarizations may appear as a single opaque ring when properly aligned, but would appear as transparent rings when misaligned. In some embodiments, the transparent rings are colorless, while the opaque ring is black.

Figure 1:
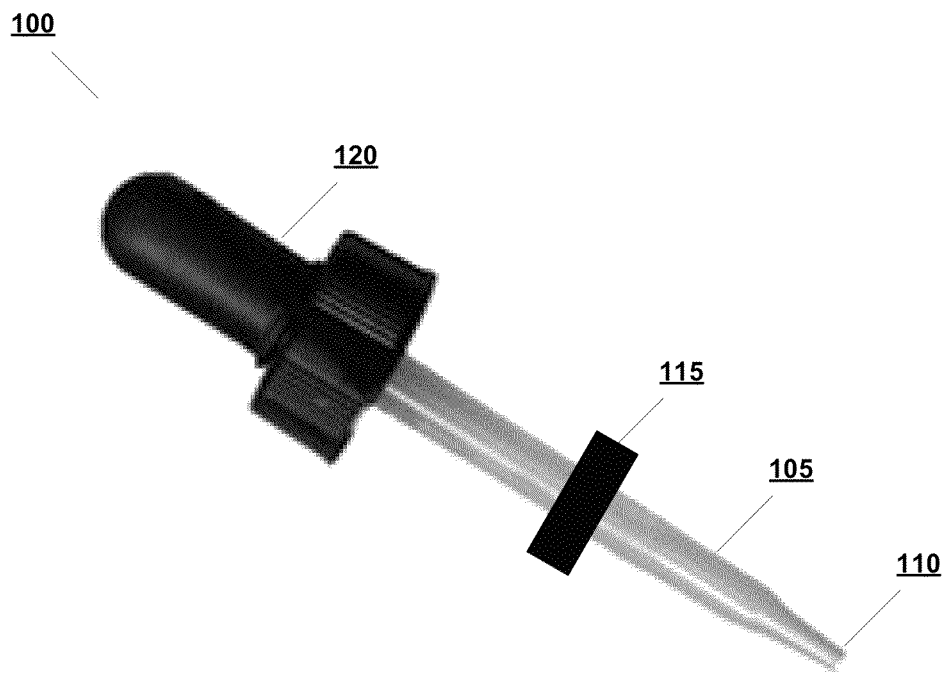
FIG. 1 depicts a side view of an illustrative dispensing unit having one concentric ring disposed around the circumference of a dispensing barrel according to an embodiment.

FIG. 1 depicts a side view of an illustrative dispensing unit having one concentric ring disposed around the circumference of a dispensing barrel according to an embodiment. As shown in FIG. 1, a dispensing unit 100 may include a dispensing barrel 105 having a dispensing orifice 110. The dispensing orifice 110 may be located at an end of the dispensing barrel 105 that is configured to be proximal to the user's eye during application of eye drops.

The dispensing unit 100 may further include one concentric ring 115 located around the circumference of the dispensing barrel 105. The concentric ring 115 may be located at a position on the dispensing barrel 105 that is distal from the dispensing orifice 110. In an embodiment, the concentric ring 115 may also be located at a position on the dispensing barrel 105 that is proximal from a reservoir 120 of the dispensing unit 100. For example, the concentric ring 115 may be placed at or around a midpoint of the dispensing barrel 105. Alternate positions for the concentric ring 115 may also be used within the scope of this disclosure.

In an embodiment, the concentric ring 115 may be translucent. In an alternate embodiment, the concentric ring 115 may be transparent. In yet another embodiment, the concentric ring 115 may be opaque.

The concentric ring 115 can generally be made of any material. Example materials include glass, plastic, polycarbonate, polypropylene, polyethylene, polyacrylate, and the like. The diameter of the ring 115 will vary in some ways according to the diameter of the dispensing barrel 105. A larger barrel diameter will lead to a larger ring diameter. In an embodiment, the ring 115 may be formed separately from the barrel and attached, adhered or otherwise positioned around the dispensing barrel 105. In an alternate embodiment, the ring 115 may be co-molded as an extension of the dispensing barrel 105.

The reservoir 120 of the dispensing unit 100 may be located at an end of the dispensing barrel 105 that is opposite to the dispensing orifice 110. The reservoir 120 may be an elastomeric bulb that is fitted to an end of the dispensing barrel 105 opposite to the dispensing orifice 110. The elastomeric bulb may be made of rubber, latex, or other elastomeric materials. When in use, the elastomeric bulb may first be compressed and the dispensing orifice 110 immersed into a volume of eye drop liquid. As the bulb decompresses, the eye drop liquid is drawn through the dispensing barrel 105 toward the reservoir 120. The dispensing unit 100 may be removed from the liquid, and the bulb can then be compressed again to dispense the eye drops through the dispensing orifice 110.

In an embodiment, the concentric ring 115 may be formed separately from the reservoir 120 and attached or adhered to the reservoir. In an alternate embodiment, the concentric ring 115 may be co-molded as part of the reservoir 120. In another embodiment, the reservoir 120 or the elastomeric bulb may include a flange that surrounds the dispensing barrel 105 with a uniform thickness to form a second larger concentric ring in addition to the concentric ring 115. The second larger concentric ring may have a diameter that is larger than that of the concentric ring 115. In an embodiment, the flange or the second larger concentric ring may be formed separately from the reservoir 120 and attached or adhered to the reservoir 120. In an alternate embodiment, the flange or the second larger concentric ring may be co-molded as part of the reservoir 120.

In an embodiment, the concentric ring 115 may have a color that differs from a color of the dispensing barrel 105. For example, the dispensing barrel 105 may be formed of a clear plastic while the concentric ring 115 may be one of black, red, green, or any other discernible color. The difference in color between the concentric ring 115 and the dispensing barrel 105 may enable a user to more readily discern the alignment of the concentric ring with respect to the dispensing barrel during a dispensing operation. Alternate colors for the dispensing barrel 105 and concentric ring 115 may be used within the scope of this disclosure.

In an embodiment, the concentric ring 115 may have a color that differs from a color of the reservoir 120. For example, the concentric ring 115 may be of a color that is discernible from the color of the flange or the second larger concentric ring. The concentric ring 115 may be attached to the flange or the second larger concentric ring, or may be located at a position on the dispensing barrel 105 that is proximal from the reservoir 120 of the dispensing unit 100. The concentric ring 115 may surround the dispensing barrel 105 with a uniform thickness that is smaller than that of the second larger concentric ring. Accordingly, the concentric ring 115 and the second larger concentric ring may surround the dispensing barrel 105 in a concentric manner, such that the concentric ring 115 forms an inner annular ring within a larger annular ring formed by the second larger concentric ring. The difference in color between the concentric ring 115 and the second larger concentric ring may enable a user to more readily discern the alignment of both rings with respect to the dispensing barrel 105 during a dispensing operation.

Figure 2A:
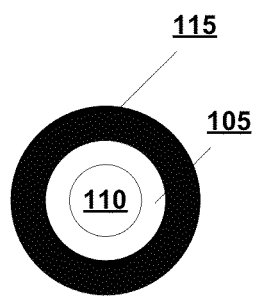
FIG. 2A depicts an illustrative view of the dispensing unit of FIG. 1 from a user's perspective when the dispensing unit is properly aligned.
Figure 2B:
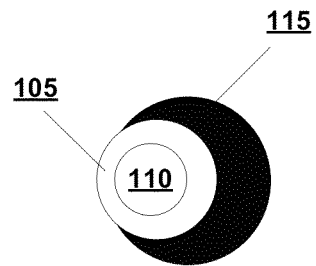
FIG. 2B depicts an illustrative view of the dispensing unit of FIG. 1 from a user's perspective when the dispensing unit is misaligned.

The concentric ring 115 may be configured to permit a user to properly visually align the dispensing barrel 105 during a dispensing operation. The user can easily and visually distinguish between a properly aligned dispensing barrel 105 and an improperly aligned dispensing barrel 105 that would more likely result in an inaccurately delivered eye drop. In an embodiment, proper alignment of the dispensing unit 100 may be achieved when the concentric ring 115 is completely visible to a user during a dispensing operation. For example, when the dispensing unit 100 is properly aligned with the eye, the concentric ring 115 may appear to completely surround the dispensing barrel 105 from the point of view of the user, such as is shown in FIG. 2A. In contrast, misalignment of the dispensing unit 100 may occur when the concentric ring 115 is not completely visible to the user. For example, when misaligned, the concentric ring 115 may only be visible around a portion of the dispensing barrel 105 from the point of view of the user, such as is shown in FIG. 2B.

The concentric ring 115 and the flange of the elastomeric bulb of the reservoir 120 may be also configured to permit a user to properly visually align the dispensing barrel 105 during a dispensing operation. In an embodiment, proper alignment of the dispensing unit 100 may be achieved when both the concentric ring 115, and an outer ring surrounding the concentric ring 115 formed by a portion of the flange not overlapping with the concentric ring 115, are completely visible to a user during a dispensing operation. For example, when the dispensing unit 100 is properly aligned with the eye, the concentric ring 115 may appear to completely surround the dispensing barrel 105, and the outer ring formed by the flange may completely surround the concentric ring 115, from the point of view of the user. In contrast, misalignment of the dispensing unit may occur when the concentric ring 115 and the outer ring surrounding the concentric ring 115 formed by the flange are not completely visible to the user. For example, when misaligned, the concentric ring 115 and the outer ring may only be visible around a portion of the dispensing barrel 105, from the point of view of the user.

Figure 3:
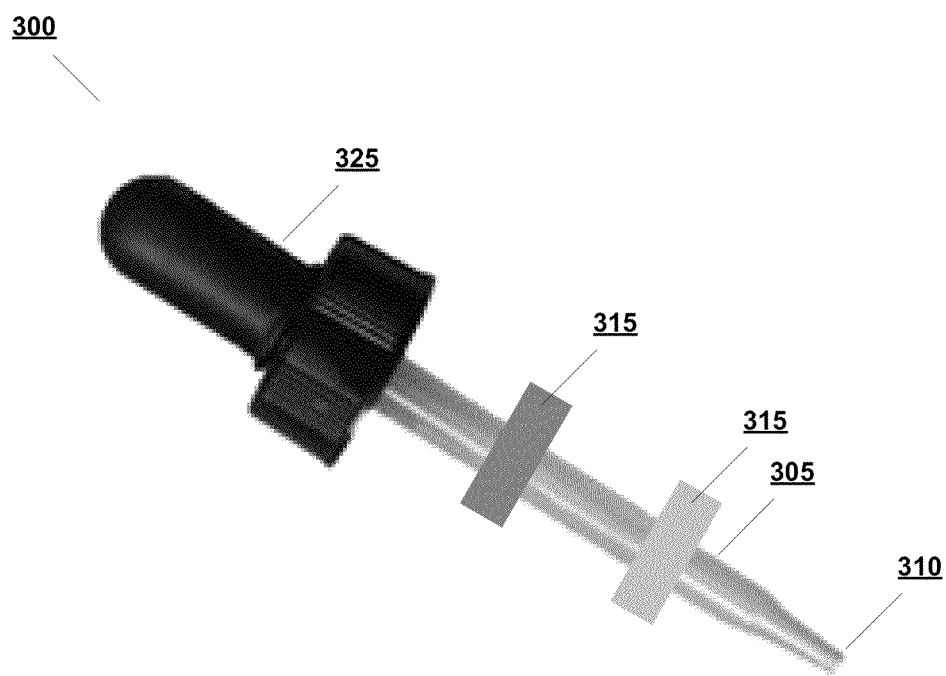
FIG. 3 depicts a side view of an illustrative dispensing unit having two concentric rings disposed around the circumference of a dispensing barrel according to an embodiment.

FIG. 3 depicts a side view of an illustrative dispensing unit having two concentric rings disposed around the circumference of a dispensing barrel according to an embodiment. As shown in FIG. 3, a dispensing unit 300 may include a dispensing barrel 305 having a dispensing orifice 310. The dispensing orifice 310 may be located at an end of the dispensing barrel 305 that is configured to be proximal to the user's eye during application of eye drops.

The dispensing unit 300 may further include a plurality of concentric rings, such as a first concentric ring 315 and a second concentric ring 320, located around the circumference of the dispensing barrel 305. The concentric rings 315 and 320 may be located at positions on the dispensing barrel 305 that are distal from the dispensing orifice 310. In an embodiment, the concentric rings 315 and 320 may also be located at positions on the dispensing barrel 305 that are proximal from a reservoir 325 of the dispensing unit 300. In an embodiment, the first concentric ring 315 may be positioned closer to the dispensing orifice 310 than the second concentric ring 320. Alternate positions for the first and second concentric rings 315 and 320 may also be used within the scope of this disclosure.

In an embodiment, the first concentric ring 315 may be translucent. In an alternate embodiment, the first concentric ring 315 may be transparent. In an embodiment, the second concentric ring 320 may be translucent. In an alternate embodiment, the second concentric ring 320 may be transparent. In yet another embodiment, the second concentric ring 320 may be opaque.

The first and second concentric rings 315, 320 can generally be made of any material. Example materials include glass, plastic, polycarbonate, polypropylene, polyethylene, polyacrylate, and the like. The diameter of the rings 315, 320 will vary in some ways according to the diameter of the dispensing barrel 305. A larger barrel diameter will lead to a larger ring diameter. In an embodiment, the rings 315, 320 may be formed separately from the barrel and attached, adhered or otherwise positioned around the dispensing barrel 305. In an alternate embodiment, the rings 315, 320 may be co-molded as an extension of the dispensing barrel 305.

The first and second concentric rings 315, 320 can have the same or different diameters from each other. In some embodiments, the first concentric ring 315 may have a smaller diameter than, substantially a same diameter as, or a larger diameter than the second concentric ring 320.

In an embodiment, the first concentric ring 315 may have a first color, and the second concentric ring 320 may have a second color that differs from the first color. For example, the first concentric ring 315 may be red, and the second concentric ring 320 may be blue. Alternate and/or additional colors may be used for the first and second concentric rings 315 and 320 within the scope of this disclosure.

Figure 4A:
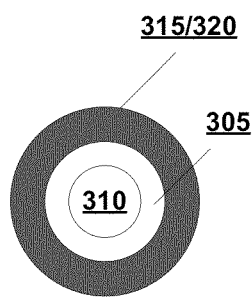
FIG. 4A depicts an illustrative view of the dispensing unit of FIG. 3 from a user's perspective when the dispensing unit is properly aligned.
Figure 4B:
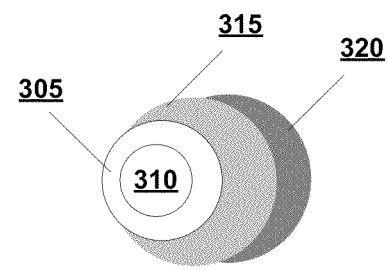
FIG. 4B depicts an illustrative view of the dispensing unit of FIG. 3 from a user's perspective when the dispensing unit is misaligned.

The first and second concentric rings 315 and 320 may be configured to permit a user to properly visually align the dispensing barrel 305 during a dispensing operation. The user can easily and visually distinguish between a properly aligned dispensing barrel 305 and an improperly aligned dispensing barrel 305 that would more likely result in an inaccurately delivered eye drop. In an embodiment, proper alignment of the dispensing unit 300 may be achieved when the first and second concentric rings 315 and 320 overlap such that a third color that results from the combination of the first color and the second color is displayed to a user. For example, when the dispensing unit 300 is properly aligned with the eye, if the first concentric ring 315 is red and the second concentric ring 320 is blue, a purple ring may appear to completely surround the dispensing barrel 305 from the point of view of the user, such as is shown in FIG. 4A. In contrast, misalignment of the dispensing unit 300 may occur when the colors of one or more of the first concentric ring 315 and the second concentric ring 320 are visible. For example, when misaligned, the color of the first concentric ring 315 and the color of the second concentric ring 320 may both be visible around a portion of the dispensing barrel 305 from the point of view of the user, such as is shown in FIG. 4B.

Where the first concentric ring 315 having a first color, and the second concentric ring 320 having a second color, are of different diameters, for example, where the first concentric ring 315 has a smaller diameter than the second concentric ring 320, proper alignment of the dispensing unit 300 may be achieved when an overlapping portion of the first concentric ring 315 with the second concentric ring 320 shows a third colored ring within the larger second concentric ring 320. For example, when the dispensing unit 300 is properly aligned with the eye, if the first concentric ring 315 is red and the second concentric ring 320 is blue, a purple ring within a blue ring may appear to completely surround the dispensing barrel 305 from the point of view of the user. Likewise, where the first concentric ring 315 has a larger diameter than the second concentric ring 320, proper alignment of the dispensing unit 300 may be achieved when an overlapping portion of the first concentric ring 315 with the second concentric ring 320 shows a third colored ring within the larger first concentric ring 315. For example, when the dispensing unit 300 is properly aligned with the eye, if the first concentric ring 315 is red and the second concentric ring 320 is blue, a purple ring within a red ring may appear to completely surround the dispensing barrel 305 from the point of view of the user.

In contrast, misalignment of the dispensing unit 300 may occur when the purple ring is not completely visible to the user. For example, when misaligned, the purple ring may only be visible around a portion of the dispensing barrel from the point of view of the user.

Figure 5:
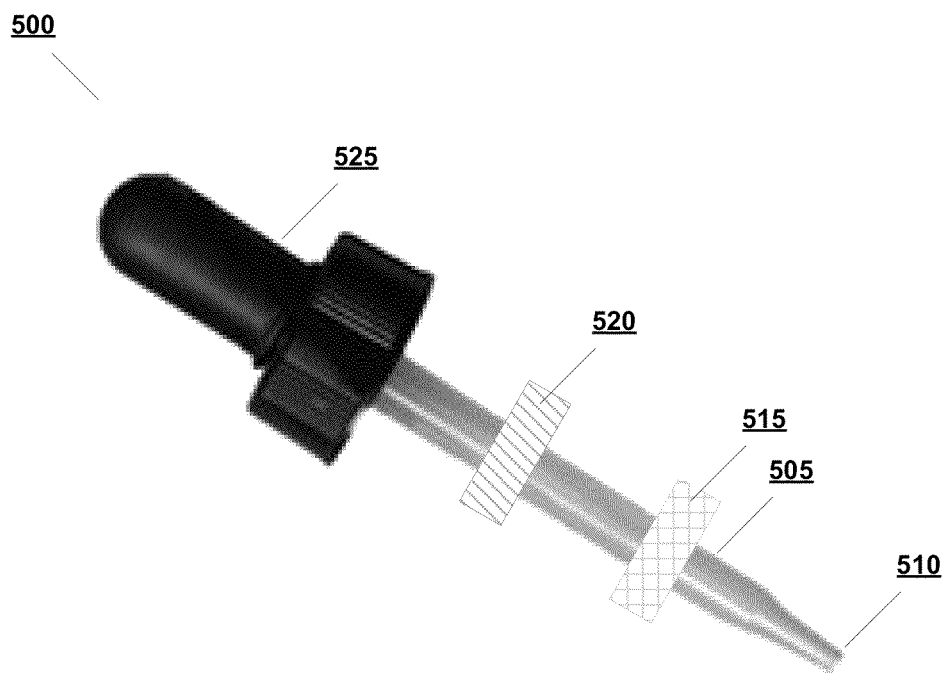
FIG. 5 depicts a side view of an illustrative dispensing unit having two concentric polarized rings disposed around the circumference of a dispensing barrel according to an embodiment.

FIG. 5 depicts a side view of an illustrative dispensing unit having two concentric polarized rings disposed around the circumference of a dispensing barrel according to an embodiment. As shown in FIG. 5, a dispensing unit 500 may include a dispensing barrel 505 having a dispensing orifice 510. The dispensing orifice 510 may be located at an end of the dispensing barrel 505 that is configured to be proximal to the user's eye during application of eye drops.

The dispensing unit 500 may further include a plurality of concentric rings, such as a first concentric ring 515 and a second concentric ring 520, located around the circumference of the dispensing barrel 505. The concentric rings 515 and 520 may be located at positions on the dispensing barrel 505 that are distal from the dispensing orifice 510. In an embodiment, the concentric rings 515 and 520 may also be located at positions on the dispensing barrel 505 that are proximal from a reservoir 525 of the dispensing unit 500. Alternate positions for the first and second concentric rings 515 and 520 may also be used within the scope of this disclosure. The first and second concentric rings 515 and 520 may generally be placed at any distance from each other along the dispensing barrel 505.

In an embodiment, the first concentric ring 515 may be translucent. In an alternate embodiment, the first concentric ring 515 may be transparent. In an embodiment, the second concentric ring 520 may be translucent. In an alternate embodiment, the second concentric ring 520 may be transparent. In an embodiment, each of the first concentric ring 515 and the second concentric ring 520 may a different optical polarization.

The first and second concentric rings 515, 520 can generally be made of any material. Example materials include glass, plastic, polycarbonate, polypropylene, polyethylene, polyacrylate, and the like. The diameter of the rings 515, 520 will vary in some ways according to the diameter of the dispensing barrel 505. A larger barrel diameter will lead to a larger ring diameter. In an embodiment, the rings 515, 520 may be formed separately from the barrel and attached, adhered or otherwise positioned around the dispensing barrel 505. In an alternate embodiment, the rings 515, 520 may be co-molded as an extension of the dispensing barrel 505.

The first concentric ring 515 and the second concentric ring 520 can have the same or different diameters from each other. In some embodiments, the first concentric ring 515 may have a smaller diameter than, substantially a same diameter as, or a larger diameter than the second concentric ring 520.

Figure 6A:
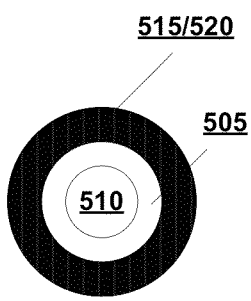
FIG. 6A depicts an illustrative view of the dispensing unit of FIG. 5 from a user's perspective when the dispensing unit is properly aligned.
Figure 6B:
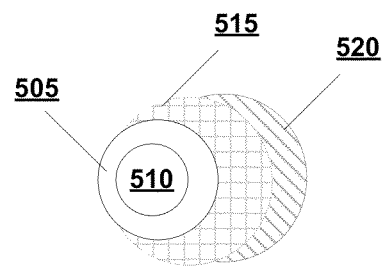
FIG. 6B depicts an illustrative view of the dispensing unit of FIG. 5 from a user's perspective when the dispensing unit is misaligned.

The first and second concentric rings 515 and 520 may be configured to permit a user to properly visually align the dispensing barrel 505 during a dispensing operation. The user can easily and visually distinguish between a properly aligned dispensing barrel 505 and an improperly aligned dispensing barrel 505 that would more likely result in an inaccurately delivered eye drop. In an embodiment, proper alignment of the dispensing unit 500 may be achieved when the first and second concentric rings 515 and 520 overlap such that the different polarizations cancel each other. For example, when the dispensing unit 500 is properly aligned with the eye, the polarizations of the first concentric ring 515 and the second concentric ring 520 may cancel each other such that a single black opaque ring may appear to completely surround the dispensing barrel 505 from the point of view of the user, such as is shown in FIG. 6A. In contrast, misalignment of the dispensing unit 500 may occur when the black ring is not visible to the user. For example, when misaligned, the black ring caused by the polarizations of the first and second concentric rings 515 and 520 may either not be visible around at least a portion of the dispensing barrel 505 from the point of view of the user, such as is shown in FIG. 6B.

Where the first concentric ring 515 having a first optical polarization, and the second concentric ring 520 having a second optical polarization, are of different diameters, for example, where the first concentric ring 515 has a smaller diameter than the second concentric ring 520, proper alignment of the dispensing unit 500 may be achieved when an overlapping portion of the first concentric ring 515 with the second concentric ring 520 shows a third ring within the larger second concentric ring 520 resulting from the cancellation of the different optical polarizations. For example, when the dispensing unit 500 is properly aligned with the eye, the polarizations of the first concentric ring 515 and the overlapped portion of the second concentric ring 520 may cancel each other such that a single black opaque ring within the larger second concentric ring 520 may appear to completely surround the dispensing barrel 505 from the point of view of the user. Likewise, where the first concentric ring 515 has a larger diameter than the second concentric ring 520, proper alignment of the dispensing unit 500 may be achieved when an overlapping portion of the first concentric ring 515 with the second concentric ring 520 shows a third colored ring within the larger first concentric ring 515. For example, when the dispensing unit 500 is properly aligned with the eye, the polarizations of the second concentric ring 520 and the overlapped portion of the first concentric ring 515 may cancel each other such that a single black opaque ring within the larger first concentric ring 515 may appear to completely surround the dispensing barrel 505 from the point of view of the user. In contrast, misalignment of the dispensing unit 500 may occur when the black ring is not completely visible to the user.

A method of using the dispensing unit as described in the disclosed embodiments may include placing the dispensing unit above the eye of a user in a dispensing configuration. The dispensing configuration may include having the dispensing barrel disposed towards the eye of the user, and aligning the dispensing unit so that the one or more concentric rings described in the disclosed embodiments may provide a visual indication of alignment above the eye of the user. The visual indication of alignment may be as described in the embodiments disclosed herein. Once the visual indication of alignment is obtained, the user may dispense one or more eye drops from the dispensing unit to the eye.

The eye drops or eye drop liquid as referred to herein may include water, saline solution, eye lubricants, or an ophthalmic medication configured for topical administration the eye. The number of drops to be dispensed or dosage of the eye drops will be dependent on the eye condition or the prescription by the doctor.

EXAMPLES

Example 1

Dispensing Unit Having Single Colored Ring

A dispensing unit having a single black ring surrounding the dispensing barrel of the dispensing unit is provided. The single black ring has a uniform outer diameter and is positioned between a plunger of the dispensing unit and a dispensing orifice. When properly positioned over a user's eye, the single black ring appears to completely surround the dispensing orifice and the dispensing barrel with a uniform thickness. Proper placement occurs when the dispensing unit is held directly above the recipient's eye with the user's head tilted backwards or with the user in a reclined position.

Example 2

Dispensing Unit Having Multiple Colored Rings

A dispensing unit having a first and second ring surrounding the dispensing barrel of the dispensing unit is provided. The first ring has a uniform outer diameter and is positioned between a dispensing orifice and the second ring. The second ring has a uniform outer diameter and is positioned between the first ring and a plunger of the dispensing unit. The first ring is transparent and is tinted a first primary color, such as blue. The second ring is tinted a second primary color, such as red. When properly positioned over a user's eye, the first and second rings overlap from the point of view of the user causing the first primary color and the second primary color to combine into a secondary color, such as purple in this example. This purple "ring" appears to completely surround the dispensing orifice and the dispensing barrel with a uniform thickness. Proper placement occurs when the dispensing unit is held directly above the recipient's eye with the user's head tilted backwards or with the user in a reclined position.

Example 3

Dispensing Unit Having Multiple Polarized Rings

A dispensing unit having a first and second ring surrounding the dispensing barrel of the dispensing unit is provided. The first ring has a uniform outer diameter and is positioned between a dispensing orifice and the second ring. The second ring has a uniform outer diameter and is positioned between the first ring and a plunger of the dispensing unit. The first ring is translucent and has a first polarization. The second ring has a second polarization that differs from the first polarization. When properly positioned over a user's eye, the first and second rings overlap from the point of view of the user. As a result, light cannot pass through both the first and second polarized rings. This causes a black "ring" to appear to completely surround the dispensing orifice and the dispensing barrel with a uniform thickness. Proper placement occurs when the dispensing unit is held directly above the recipient's eye with the user's head tilted backwards or with the user in a reclined position.

Example 4

Delivery of Eye Drop Using Dispensing Unit Having One Ring

A user reclines in a prone position and places the dispensing unit above the eye into which the eye drops are to be placed. The dispensing unit includes a dispensing barrel and a concentric ring. The dispensing unit is placed in a dispensing configuration (i.e., such that the dispensing unit has a dispensing barrel disposed towards the eye of the user). The dispensing unit is aligned by the user so that the concentric ring provides a visual indication of alignment above the user's eye. Specifically, the visual indication is achieved by having the concentric ring completely visible to the user. One or more eye drops are then dispensed from the dispensing unit to the eye of the user. The exact dosage may be prescribed by a doctor or printed on the dispensing unit or packaging associated with the dispensing unit. Using this method it is expected that a more accurate delivery of the eye drops to the eye of the user is achieved that with conventional eyedroppers.

Example 5

Delivery of Eye Drop Using Dispensing Unit Having Multiple Colored Rings

A user reclines in a prone position and places the dispensing unit above the eye into which the eye drops are to be placed. The dispensing unit includes a dispensing barrel, a red concentric ring and a blue concentric ring. The dispensing unit is placed in a dispensing configuration (i.e., such that the dispensing unit has a dispensing barrel disposed towards the eye of the user). The dispensing unit is aligned by the user so that the red and blue concentric rings appear to produce a single purple ring from the perspective of the user. One or more eye drops are then dispensed from the dispensing unit to the eye of the user. The exact dosage may be prescribed by a doctor or printed on the dispensing unit or packaging associated with the dispensing unit. Using this method it is expected that a more accurate delivery of the eye drops to the eye of the user is achieved that with conventional eyedroppers.

Example 6

Delivery of Eye Drop Using Dispensing Unit Having Multiple Polarized Rings

A user reclines in a prone position and places the dispensing unit above the eye into which the eye drops are to be placed. The dispensing unit includes a dispensing barrel and two concentric rings having different polarizations. The dispensing unit is placed in a dispensing configuration (i.e., such that the dispensing unit has a dispensing barrel disposed towards the eye of the user). The dispensing unit is aligned by the user so that the concentric rings appear to produce a single black ring from the perspective of the user. One or more eye drops are then dispensed from the dispensing unit to the eye of the user. The exact dosage may be prescribed by a doctor or printed on the dispensing unit or packaging associated with the dispensing unit. Using this method it is expected that a more accurate delivery of the eye drops to the eye of the user is achieved that with conventional eyedroppers.

Example 7

Dispensing Unit Having a Single Colored Ring Attached to a Plunger of the Dispensing Unit A dispensing unit is provided having a single black ring surrounding a dispensing barrel. The dispensing barrel has a plunger at one end and a dispensing orifice an opposite end. The plunger is an elastomeric bulb having a flange that surrounds the dispensing barrel with a first uniform thickness. The bulb with the flange is red in color. The single black ring surrounding the dispensing barrel is attached to the flange, and is positioned between the plunger and the dispensing orifice. The single black ring surrounds the dispensing barrel with a second uniform thickness that is smaller than the first uniform thickness. The single black ring is adhered to the flange of the elastomeric bulb such that the flange and the black ring surrounds the dispensing barrel in a concentric manner. Accordingly, the single black ring will form an inner annular ring within a larger red annular ring formed by the red flange. When the dispensing unit is properly aligned over a user's eye, a full black ring that appears to completely surround the dispensing barrel with uniform thickness, and a full red ring that appears to completely surround the black ring with uniform thickness, will be visible from the point of view of the user. In contrast, when the dispensing unit is not properly aligned, the full black ring and the full red ring will not be completely visible from the point of view of the user. For example, the black and red rings will only be visible around a portion of the dispensing barrel, or both rings will not appear to have a uniform thickness around the dispensing barrel.

Example 8

Delivery of Eye Drop Using Dispensing Unit Having a Single Colored Ring Attached to a Plunger of the Dispensing Unit A user reclines in a prone position and places the dispensing unit of Example 7 above the eye into which the eye drops are to be placed. The alignment of the dispensing unit is adjusted by the user until a full black ring that appears to completely surround the dispensing barrel with uniform thickness, and a full red ring that appears to completely surround the black ring with uniform thickness, are visible from the point of view of the user. This provides a visual indication to the user that the dispensing unit is properly aligned. One or more eye drops are then dispensed from the dispensing unit to the eye of the user. Using this method, it is expected that a more accurate delivery of the eye drops to the eye of the user is achieved than can be achieved using conventional eyedroppers.

Example 9

Prototype of a Dispensing Unit Having a Single Colored Ring

A dispensing unit having a single blue ring disposed around a circumference of a dispensing barrel was manufactured. The dispensing barrel had a plunger at one end and a dispensing orifice at an opposite end. The blue ring was positioned between the plunger and the dispensing orifice. The dispensing barrel and the dispensing orifice formed an integral structure made of a 20 ml capillary glass tube having a portion that tapered toward the dispensing orifice. The glass tube had a length of 100 mm, with the tapering portion forming about 25 mm of the length. The diameter of the glass tube was 7 mm, which tapered along the tapering portion to 1.5 mm at the dispensing orifice. The plunger was made of a latex bulb fitted to the glass tube at an opposite end from the dispensing orifice. When in use, the latex bulb contained a reservoir of eye drop liquid which can be dispensed when the bulb is compressed. The blue ring was made of polyacrylate that was tinted blue, and was transparent. The blue ring was laser cut to size, and surrounded the glass tube with a uniform thickness of 6 mm. The blue ring had an outer diameter of 19 mm, and an inner diameter of 7 mm. The blue ring was positioned along the glass tube at about 70 mm from the dispensing orifice. Loctite® 4011™ adhesive (Henkel Corporation; Rocky Hill, Conn. 06067, USA) was applied to the interface between the blue ring and the glass tube to affix the blue ring to the glass tube. The dispensing unit was used by a user who was in a reclined position. When the dispensing unit was properly aligned over the user's eye, a full single blue ring that appeared to completely surround the dispensing barrel with a uniform thickness, was visible from the point of view of the user. In contrast, when the dispensing unit was not properly aligned, the full single blue ring was not completely visible from the point of view of the user. For example, the blue ring was only visible around a portion of the dispensing barrel, or the blue ring did not appear to have a uniform width around the dispensing barrel.

Example 10

Prototype of a Dispensing Unit Having Multiple Colored Rings

A dispensing unit having a first yellow ring and a second blue ring disposed around a circumference of a dispensing barrel was manufactured. The dispensing barrel had a plunger at one end and a dispensing orifice at an opposite end. The first yellow ring was positioned between the dispensing orifice and the second blue ring. The second blue ring was positioned between the plunger and the first yellow ring. The dispensing barrel and the dispensing orifice formed an integral structure made of a 20 ml capillary glass tube having a portion that tapered toward the dispensing orifice. The glass tube had a length of 100 mm, with the tapering portion forming 25 mm of the length. The diameter of the glass tube was 7 mm, which tapered along the tapering portion to 1.5 mm at the dispensing orifice. The plunger was made of a latex bulb fitted to the glass tube at an opposite end from the dispensing orifice. When in use, the latex bulb contained a reservoir of eye drop liquid which can be dispensed when the bulb is compressed. The first ring was made of yellow tinted polyacrylate, and the second ring was made of blue tinted polyacrylate. Both the yellow and blue rings were transparent. Each of the yellow ring and the blue ring was laser cut to size, and surrounded the glass tube with a uniform thickness of 6 mm. Both the yellow ring and the blue ring had an outer diameter of 19 mm, and an inner diameter of 7 mm. The yellow ring was positioned along the glass tube at about 50 mm from the dispensing orifice, and the blue ring was positioned along the glass tube at about 70 mm from the dispensing orifice. Loctite® 4011™ adhesive (Henkel Corporation; Rocky Hill, Conn. 06067, USA) was applied to the interface between each of the yellow and blue rings and the glass tube to affix both rings to the glass tube. The dispensing unit was used by a user who was in a reclined position. When the dispensing unit was properly aligned over the user's eye, a full single "green" ring that appeared to completely surround the dispensing barrel with a uniform thickness, was visible from the point of view of the user. The "green" ring was a result of the first yellow ring and the second blue ring overlapping from the point of view of the user causing the two colors to combine into a new third color, green. In contrast, when the dispensing unit was not properly aligned, the yellow color of the first yellow ring, the blue color of the second blue ring, and a green region resulting from a partial overlap between the two colors, were visible around a portion of the dispensing barrel from the point of view of the user.

Example 11

Delivery of Eye Drop Using a Conventional Eye Dropper

A conventional eye dropper having a similar configuration as Example 9 and Example 10 was provided, but without the colored ring or rings. In a reclined position, a user had placed the conventional eye dropper over an eye, and adjusted the eye dropper until the dispensing orifice appeared to be above the eye from the point of view of the user. About three drops of the eye drop liquid were then dispensed from the conventional eye dropper. It was observed that two out of the three drops of the eye drop liquid had missed the eye, resulting in wastage of the eye drop liquid.

Example 12

Delivery of Eye Drop Using the Prototype from Example 9

A user had used the dispensing unit from Example 9 in a reclined position. The dispensing unit was placed above an eye of the user, and the alignment of the dispensing unit was adjusted until the user saw a blue ring that surrounded the dispensing orifice and the dispensing barrel with a uniform thickness, and the blue ring was completely visible to the user. This was a visual indication to the user that the dispensing unit was properly aligned. About three drops of the eye drop liquid were then dispensed from the dispensing unit to the eye of the user when the user compressed the latex bulb. It was observed that all three drops of the eye drop liquid were delivered to the eye and none of the drops had missed the eye. It will therefore be appreciated that the dispensing unit having a single colored ring disposed around a circumference of the dispensing barrel as described in the embodiments disclosed herein, had provided better accuracy in delivering eye drop liquid to the eye than the conventional eye dropper.

Example 13

Delivery of Eye Drop Using the Prototype from Example 10

A user had used the dispensing unit from Example 10 in a reclined position. The dispensing unit was placed above an eye of the user, and the alignment of the dispensing unit was adjusted until the user saw a complete "green" ring that surrounded the dispensing orifice and the dispensing barrel with a uniform thickness. This was a visual indication to the user that the dispensing unit was properly aligned. About three drops of the eye drop liquid were then dispensed from the dispensing unit to the eye of the user when the user compressed the latex bulb. It was observed that all three drops of the eye drop liquid were delivered to the eye and none of the drops had missed the eye. It will therefore be appreciated that the dispensing unit having multiple colored rings disposed around a circumference of the dispensing barrel as described in the embodiments disclosed herein, had provided better accuracy in delivering eye drop liquid to the eye than the conventional eye dropper.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A dispensing unit comprising:
   a dispensing barrel having a dispensing orifice;
   a reservoir disposed at an end of the dispensing barrel opposite to the dispensing orifice;

a first ring disposed around the dispensing barrel; and a second ring disposed around the dispensing barrel, wherein the first ring is located at a position on the dispensing barrel that is between the dispensing orifice and the second ring, and wherein the second ring is larger in diameter than the first ring.

2. The dispensing unit of claim 1, wherein the second ring is located between the reservoir and the first ring.

3. The dispensing unit of claim 1, wherein the first ring is translucent or transparent.

4. The dispensing unit of claim 1, wherein the first ring has a color that differs from a color of the dispensing barrel.

5. The dispensing unit of claim 1, wherein the first ring is affixed to the dispensing barrel, adhered to the dispensing barrel, or molded as part of the dispensing barrel.

6. The dispensing unit of claim 1, wherein the second ring is affixed to, adhered to, or molded as part of the reservoir.

7. The dispensing unit of claim 1, wherein the first ring has a color that differs from a color of the second ring.

8. The dispensing unit of claim 1, wherein the first ring and the second ring are configured to permit a user to properly visually align the dispensing barrel when the first ring and an outer ring formed by a portion of the second ring not overlapping with the first ring are completely visible to a user during a dispensing operation through the dispensing orifice.

9. A dispensing unit comprising:

a dispensing barrel having a dispensing orifice;

a reservoir disposed at an end of the dispensing barrel opposite to the dispensing orifice; and a plurality of rings disposed around the dispensing barrel, wherein the plurality of rings comprise a first ring and a second ring, wherein the first ring is located at a position on the dispensing barrel that is between the dispensing orifice and the second ring, and wherein the plurality of rings are configured to permit a user to properly visually align the dispensing barrel above an eye of the user.

10. The dispensing unit of claim 9, wherein the plurality of rings have substantially equal diameters.

11. The dispensing unit of claim 9, wherein the first ring has a first color and the second ring has a second color.

12. The dispensing unit of claim 11, wherein the plurality of rings are configured to permit a user to properly visually align the dispensing barrel by aligning the first and second rings such that a user perceives a complete ring having a third color, wherein the third color comprises a combination of the first color and the second color.

13. The dispensing unit of claim 9, wherein each of the first and second rings are clear and polarized, wherein the polarization of the first ring differs from the polarization of the second ring.

14. The dispensing unit of claim 13, wherein the plurality of rings are configured to permit a user to properly visually align the dispensing barrel by aligning the first and second rings such that a user perceives a complete dark ring, wherein the complete dark ring results from the differing polarization of the first and second rings.

15. The dispensing unit of claim 9, wherein at least one of the plurality of rings is affixed to, adhered to, or molded as part of the dispensing barrel.

16. The dispensing unit of claim 9, wherein the reservoir comprises a flange having a diameter that is larger than a diameter of each of the plurality of rings.

17. The dispensing unit of claim 16, wherein the flange has a color that differs from a color of each of the plurality of rings.

18. The dispensing unit of claim 16, wherein the first and second rings and the flange are configured to permit a user to properly visually align the dispensing barrel when the first and second rings and an outer ring formed by a portion of the flange not overlapping with either of the first ring or the second ring are completely visible to a user during a dispensing operation through the dispensing orifice.

19. A dispensing unit comprising:

a dispensing barrel having a dispensing orifice;

a reservoir disposed at an end of the dispensing barrel opposite to the dispensing orifice; and a ring disposed around a circumference of the dispensing barrel, wherein the reservoir comprises a flange having a radius that is larger than a radius of the ring, and wherein the ring is located at a position on the dispensing barrel that is between the flange and the dispensing orifice.

20. The dispensing unit of claim 19, wherein the ring has a color that differs from a color of the dispensing barrel.

21. The dispensing unit of claim 19, wherein the ring is affixed to the dispensing barrel, adhered to the dispensing barrel, or molded as part of the dispensing barrel.

22. The dispensing unit of claim 19, wherein the flange has a color that differs from a color of the ring.

23. The dispensing unit of claim 19, wherein the ring and the flange are configured to permit a user to properly visually align the dispensing barrel when the ring and an outer ring formed by a portion of the flange not overlapping with the ring are completely visible to a user during a dispensing operation through the dispensing orifice.

* * * * *